US010002311B1

(12) United States Patent
Garnavi et al.

(10) Patent No.: US 10,002,311 B1
(45) Date of Patent: Jun. 19, 2018

(54) GENERATING AN ENRICHED KNOWLEDGE BASE FROM ANNOTATED IMAGES

(71) Applicant: International Business Machines Corporation, Armonk, NY (US)

(72) Inventors: Rahil Garnavi, Macleod (AU); Dwarikanath Mahapatra, Travancore (AU); Suman Sedai, Melbourne (AU); Ruwan B. Tennakoon, Hawthorn (AU)

(73) Assignee: International Business Machines Corporation, Armonk, NY (US)

( * ) Notice: Subject to any disclaimer, the term of this patent is extended or adjusted under 35 U.S.C. 154(b) by 0 days. days.

(21) Appl. No.: 15/429,735

(22) Filed: Feb. 10, 2017

(51) Int. Cl.
*G06K 9/00* (2006.01)
*G06K 9/62* (2006.01)
*G06K 9/46* (2006.01)
*G10L 15/26* (2006.01)
*G06F 19/00* (2018.01)
(Continued)

(52) U.S. Cl.
CPC ......... *G06K 9/6254* (2013.01); *G06F 19/321* (2013.01); *G06K 9/00604* (2013.01); *G06K 9/4604* (2013.01); *G06K 9/6256* (2013.01); *G06K 9/6263* (2013.01); *G06N 3/0427* (2013.01); *G06N 3/0445* (2013.01);
(Continued)

(58) Field of Classification Search
CPC .......... G06T 19/006; G02B 2027/0138; G02B 2027/014; G02B 2027/0141; G02B 2027/0178; G02B 2027/0187; G02B 27/0093; G02B 27/017; G02B 27/0172; G06F 21/32; G06F 2203/011; G06F 3/013; G06F 3/017; G06F 3/0236; G06F 3/0304; G06F 3/04845; G06F 3/04
USPC .................................................. 382/128, 103
See application file for complete search history.

(56) References Cited

U.S. PATENT DOCUMENTS 6,991,464 B2  1/2006  Liebert
7,052,277 B2  5/2006  Kellman
(Continued)

OTHER PUBLICATIONS

The University of Sydney, "Virtual Ophthalmology Clinic", http://sydney.edu.au/medicine/eye/virto/web2-singlecase/, Accessed on Feb. 1, 2017, 1 page.
(Continued)

*Primary Examiner* — Tom Y Lu
(74) *Attorney, Agent, or Firm* — Scully, Scott, Murphy & Presser, P.C.; Louis J. Percello, Esq.

(57) ABSTRACT

A knowledge base is generated based on eye tracking, audio monitoring and image annotations, for determining image features from given images and sequences of image features to focus on in analyzing an image. An eye tracker monitors eye movements of a user analyzing an image and generates a sequence of eye movements. A user interface receives annotations on the image. Audio data received via a microphone is translated into text and keywords are extracted. The sequence of eye movements, the annotations and the keywords are correlated according to their time of occurrence. Image features are extracted from the image and mapped with the sequence of eye movements, the annotations and the keywords that are correlated. A recurrent neural network model is generated based on the mapped image features and predicts a likelihood of an expert image analyzer focusing on a feature in a given new image.

20 Claims, 7 Drawing Sheets

(51) Int. Cl.
  *G09B 23/28* (2006.01)
  *G06N 3/04* (2006.01)
  *G06N 3/08* (2006.01)
(52) U.S. Cl.
  CPC .............. *G06N 3/08* (2013.01); *G09B 23/28* (2013.01); *G10L 15/265* (2013.01)

(56) References Cited

U.S. PATENT DOCUMENTS

| | | | |
|---|---|---|---|
| 8,811,657 | B2 | 8/2014 | Teiwes et al. |
| 9,039,419 | B2 | 5/2015 | Dietrich et al. |
| 9,423,870 | B2 | 8/2016 | Teller et al. |
| 2011/0270123 | A1 | 11/2011 | Reiner |
| 2013/0137076 | A1 | 5/2013 | Perez et al. |
| 2014/0156827 | A1* | 6/2014 | Mankovskii ...... H04L 29/08099 709/224 |
| 2015/0009118 | A1 | 1/2015 | Thomas et al. |
| 2017/0123492 | A1* | 5/2017 | Marggraff ............. G06F 3/0236 |
| 2017/0308654 | A1* | 10/2017 | Luz Rello-Sanchez ....... G06N 7/005 |
| 2018/0032031 | A1* | 2/2018 | Du .......................... G03H 1/28 |

OTHER PUBLICATIONS

Succar, T., et al., "The impact of the Virtual Ophthalmology Clinic on medical students' learning: a randomised controlled trial", Eye (2013), Jul. 2013, pp. 1151-1157, vol. 27.

Khanna, A., "EyeSim—Medical Traning for Opthalmology", EON Reality Inc., http://www.eonreality.com/portfolio-items/eyesim/, Accessed on Feb. 1, 2017, 6 pages.

Gribova, V.V., et al., "Computer teaching simulator with virtual reality for ophthalmology", The 9th International Conference on Information Technology and Applications (ICITA 2014), Jul. 2014, 3 pages.

Weller, J.M., et al., "Simulation in clinical teaching and learning", Medical Journal of Australia, May 2012, p. 594, vol. 196, No. 9.

Nodine, C.F., et al., "How Experience and Training Influence Mammography Expertise", Academic Radiology, Oct. 1999, pp. 575-585, vol. 6, No. 10.

Speelman, C., et al., "Skill Acquisition in Skin Cancer Detection", Perceptual and Motor Skills, pp. 277-297, vol. 110, No. 1.

Sherbino, J., et al., "The Relationship Between Response Time and Diagnostic Accuracy", Academic Medicine, Jun. 2012, pp. 785-791, vol. 87, No. 6.

Krasne, S., et al., "Applying perceptual and adaptive learning techniques for teaching introductory histopathology", Journal of Pathology Informatics, Dec. 2013, 8 pages, vol. 4, No. 34.

Zou, X, et al., "Learning-Based Visual Saliency Model for Detecting Diabetic Macular Edema in Retinal Image", Computational Intelligence and Neuroscience, Hindawai Publishing Corporation, Dec. 2015, 10 pages, vol. 2016, Article ID 7496735.

Helbren, E., et al., Towards a framework for analysis of eye-tracking studies in the three dimensional environment: a study of visual search by experienced readers of endoluminal CT colonography, The British Journal of Radiology, Feb. 2014, 6 pages, vol. 87, No. 1037.

Krupinski, E., et al., "Eye Tracking Helps Improve Accuracy in Radiology", BioPhotonics, Jun. 2006, https://www.photonics.com/Article.aspx?AID=43855, Accessed on Feb. 1, 2017, 9 pages.

Mallett, S., et al., "Tracking Eye Gaze during Interpretation of Endoluminal Three-dimensional CT Colonography: Visual Perception of Experienced and Inexperienced Readers", Radiology, Dec. 2014, pp. 783-792, vol. 273, No. 3.

Meining, A., et al., ""Eye-tracking" for assessment of image perception in gastrointestinal endoscopy with narrow-band imaging compared with white-light endoscopy", Endoscopy 2010, Jun. 2010, pp. 652-655, vol. 42.

Dennies, E., et al., "Investigating the Use of Eye-Tracking Technology for Assessment—A case study of research and innovation at Nether Hall Special School", Full Research Report, Dec. 2015, 39 pages.

Malcolm, G.L., "Combining top-down processes to guide eye movements during real-world scene search", Journal of Vision (2010), Feb. 2010, pp. 1-11, vol. 10(2):4.

Okekoya, O., et al., "An Eye Tracking Interface for Image Search", Proceedings of the 2006 symposium on Eye tracking research & applications (ETRA '06), Mar. 2006, 1 page.

Seiple, W., et al., "Eye-Movement Training for Reading in Patients with Age-Related Macular Degeneration", Investigative Ophthalmology & Visual Science, Aug. 2005, pp. 2886-2896, vol. 46, No. 8.

Perry, L., "UCLA study shows eye-tracking technology improves nursing training", UCLA Newsroom, Aug. 15, 2016, http://newsroom.ucla.edu/releases/ucla-study-shows-eye-tracking-technology-improves-nursing-training, Accessed on Feb. 1, 2017, 3 pages.

Van Den Bogert, N., "On teachers' visual perception and interpretation of classroom events using eye tracking and collaborative tagging methodologies", Technische Universiteit Eindhoven, Jan. 2016, 130 pages.

Cooper, S., et al., "Can eye-tracking technology improve situational awareness and student feedback during simulation?", Final Report 2014, http://emergencyeyetracking.com/wp-content/uploads/2013/12/SD12-2432_Monash_Cooper_Final-Report.pdf, Accessed on Feb. 1, 2017, 39 pages.

John, B., et al., "Collaborative Eye Tracking for Image Analysis", ETRA 2014, Mar. 2014, pp. 239-242.

Ciotti, G., "7 Marketing Lessons from Eye-Tracking Studies", Kissemtrics Blog, https://blog.kissmetrics.com/eye-tracking-studies/, Accessed on Feb. 1, 2016, 16 pages.

Sensomotoric Instruments (SMI), "Case Study: Eye Tracking & Teachers' Classroom Perception", http://www.smivision.com/en/gaze-and-eye-tracking-systems/applications/psychology-psychiatry-psycholinguistics/teachers-classroom-perception.html, Accessed on Feb. 6, 2017, 2 pages.

TOBII PRO, "Educational Research", http://www.tobiipro.com/fields-of-use/education/educational-research/, Accessed on Feb. 1, 2017, 3 pages.

Li, K., et al., "Promoting Learning Attention with Gaze Tracking Integrated e-Learning Contents", Knowledge-Based and Intelligent Information and Engineering Systems, 14th International Conference KES 2010, Proceedings Part IV, Sep. 2010, pp. 173-179, Lecture Notes in Computer Science vol. 6279.

Sinclair, M.A. "Inspection of Rolls in Roller Bearings, Advances in Psychology, Theoretical and Applied Aspects of Eye Movement Research", Sep. 1983, Published 1984, pp. 373-379, vol. 22.

Dhein, C.R., et al., "Teaching the Didactic Aspects of Opthalmology and Dermatology Using an off-Site Instructor", Journal of Veterinary Medical Education, Feb. 2005, pp. 57-67, vol. 32, No. 1.

Kuchenbecker, J., et al., "Internet-based teaching and learning in opthalmology", Opthalmology, Oct. 2001, 6 pages, vol. 98, No. 10, with English Language abstract.

* cited by examiner

GENERATING AN ENRICHED KNOWLEDGE BASE FROM ANNOTATED IMAGES

FIELD

The present application relates generally to computers and computer applications, and more particularly to image processing, learning image features, and constructing computer knowledgebase.

BACKGROUND

Image analysis for decision making is an important component of many tasks such as medical diagnosis, industrial applications and satellite image interpretation. Human observers rely on their own and others' acquired knowledge and experience to annotate and interpret images. It is important to train novice observers adequately so that they can perform these tasks competently. An important component of this training is the availability of human experts to train novices. However it is difficult to find adequate number of qualified experts to impart training to others.

An example case in point is retinal image analysis for pathology detection. Diagnosis and management of retinal conditions such as diabetic retinopathy (DR) or Age related macular Degeneration (AMD) is important as they are one of the leading causes of blindness in the world. DR is a complication of diabetes and AMD is a complication of advancing age. With the increasing number of such patients around the world, it is important to have clinicians who are adequately trained to detect incidence of DR and AMD, and recommend appropriate action. Training ophthalmologists is a resource intensive procedure that requires considerable time and effort from experienced ophthalmologists and clinicians. Such training may be relatively easier to impart in urban clinics which has higher number of trained clinicians. However, such resources are not available in remote areas and therefore patients residing in remote areas are at a severe disadvantage due to lack of access to clinicians and other facilities.

Recently tele-ophthalmology has emerged as a possible solution where retinal scans are taken at remote locations using relatively inexpensive hardware and are transmitted to a central server to be assessed by ophthalmologists. Once the assessment is completed a report is sent back to the remote clinic. Commonly, tele-ophthalmology programs are monitored by inexperienced clinicians who may not be trained in severity assessment but have basic training in operating the equipment. Although this approach has improved the access to clinics for people in remote locations it also suffers from the following limitations:

Considerable time is spent from the time a patient's image is acquired to getting a report from an expert. Due to this delay the following incidents are frequently observed: a) the patient does not return for a follow up check; and b) retinal conditions may change rapidly for the worse. The consistency of the grading is not guaranteed as images from the same location or of the same patient may not be analyzed by the same expert.

Referring to the ophthalmology case example, irrespective of the fact whether the clinician is in a urban or remote setting, the inventors in this disclosure have recognized that training ophthalmologists requires the following of a set of formal guidelines. For instance, the inventors in this disclosure have recognized that the above issues can be addressed to a significant degree if there exists a training module for ophthalmologists that can performs the functions such as: 1) Assists operators in learning to identify the relevant patterns necessary to detect retinal pathologies without direct supervision of experts; 2) Suggests locations of interest (pathologies) to the less experienced grader using automatic algorithms to ensure consistency; 3) Provides feedback on the operators' proficiency and identify areas where further training is required, by comparing their detections with the detections of an automatic algorithm. The inventors in this disclose have also recognized that such a system should output consistent results in order to reduce bias due to subjectivity.

BRIEF SUMMARY

A system and method of generating a knowledge base from annotated images are provided. The system, in one aspect, may include a hardware processor executing a user interface, the hardware processor retrieving an image from a database of images and presenting the image on the user interface displayed on a display device. An eye tracker may include at least a camera and coupled to the hardware processor, the eye tracker monitors eye movements of a user analyzing the image and generates a sequence of eye movements. The user interface receives annotations on the image input by the user. The hardware processor receives via the microphone audio data associated with the image spoken by the user, the hardware processor translating the audio data into text, and extracting keywords from the text. The hardware processor correlates the sequence of eye movements, the annotations and the keywords according to their time of occurrence. The hardware processor extracts image features from the image and maps the image features with the sequence of eye movements, the annotations and the keywords that are correlated. The hardware processor generates a recurrent neural network model that predicts a likelihood of an expert image analyzer focusing on a feature in a given new image, for example, based on mappings of the image features with the sequence of eye movements, the annotations and the keywords that are correlated. A knowledgebase stores the recurrent neural network model and the mappings of the image features with the sequence of eye movements, the annotations and the keywords that are correlated.

A method of generating a knowledge base from annotated images, in one aspect, may include retrieving an image from a database of images and presenting the image on a user interface displayed on a display device. The method may also include transmitting a signal to an eye tracker comprising at least a camera coupled to the hardware processor, the signal representing a notification to the eye tracker to monitor eye movements of a user analyzing the image and generating a sequence of eye movements based on the eye tracker monitor the eye movements. The method may further include receiving via the user interface, annotations on the image input by the user. The method may also include receiving via a microphone coupled to the hardware processor, audio data associated with the image spoken by the user, and translating the audio data into text, and extracting keywords from the text. The method may also include correlating the sequence of eye movements, the annotations and the keywords according to their time of occurrence. The method may further include extracting image features from the image and mapping the image features with the sequence of eye movements, the annotations and the keywords that are correlated. The method may also include generating a recurrent neural network model that predicts a likelihood of an expert image analyzer focusing on a feature in a given new image, the generating the recurrent neural network model based on mappings of the image features with the sequence of eye movements, the annotations and the keywords that are correlated. The method may also include storing in a knowledgebase, the recurrent neural network model and the mappings of the image features with the sequence of eye movements, the annotations and the keywords that are correlated.

A computer readable storage medium storing a program of instructions executable by a machine to perform one or more methods described herein also may be provided.

Further features as well as the structure and operation of various embodiments are described in detail below with reference to the accompanying drawings. In the drawings, like reference numbers indicate identical or functionally similar elements.

DETAILED DESCRIPTION

A system and set of methods are disclosed that build an enriched knowledge base from annotated images. The system and methods may also extract the relevant knowledge to help in identifying mistakes and ways to better understand the experts' insights. The system and methods are described using ophthalmology as a use case although the system and methods are relevant for other application domains such as satellite image analysis, industrial inspection systems, and/or others, not limited to diagnostic ophthalmology learning and knowledgebase. In the diagnosis of diabetic retinopathy (DR) the system of the present disclosure in one embodiment captures knowledge on DR diagnosis (or any other disease) and severity estimation from expert ophthalmologists and model it such that it can be used in effective training of new ophthalmologists/graders. The learned information in one embodiment includes image patterns for DR classification, search strategy of an expert in identifying DR, audio cues, time taken by the experts to analyze image regions and expert consistency.

For example, a system in one embodiment creates a knowledge base from the input of expert ophthalmologists. This knowledge base may be used to train less experienced graders, and improve their skills so they can analyze retinal images. In one embodiment, the knowledge base is created by taking input from the following input sources of clinical experts: 1) eye tracking data; 2) audio cues; 3) image annotations.

In one embodiment, a system captures expert knowledge on image analysis by tracking visual attention, voice cues and annotations. The system trains a transition model of visual attention based on sequence learning and stores the model in knowledgebase. The system also computes difficulty and importance of a case and observed interesting regions based on image features, audio cues and time taken by expert.

Examples of advantages the system and methods of the present disclosure have over the existing perceptual training systems include, but are not limited to the following: The use of eye tracking information and audio cues in combination with learner image features facilitate the learner to grasp additional information that would not be available with image only perceptual learning systems; The creation of a knowledge base (or oracle) enables the teaching module to present the most important information to the learner for the relevant task. It also enables to generalize the expert knowledge to previously unseen images. Therefore, the evaluation module can be used as a reference against which a novice grader can evaluate his or her findings.

Figure 1:
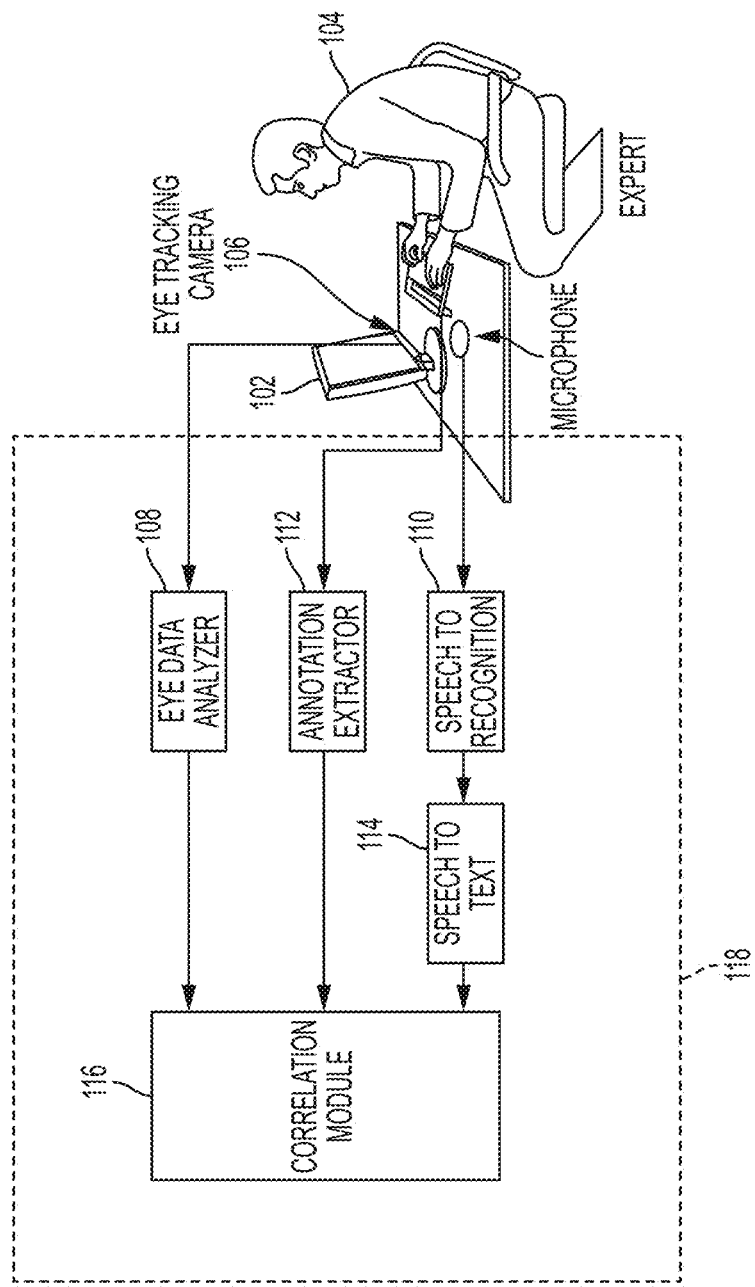
FIG. 1 illustrates high level system components in one embodiment of the present disclosure.

FIG. 1 illustrates high level system components in one embodiment of the present disclosure that constructs an enriched knowledge base. At least one hardware processor 118 executes the components shown in FIG. 1, for example, a user interface program or software, an eye data analyzer 108, annotation extractor 112, speech recognition 110, speech to text conversion 114 and correlation 116. An eye tracker such as an eye tracking camera 106 is coupled to the hardware processor An image initially stored into the knowledge base is presented through a user interface (UI) 102 on a visual display device, via to an expert or like user 104. An eye-gaze-tracker, e.g., an eye tracking camera 106, or another hardware that includes a lens component and a processor component, is notified that a new image is made available and a reference code is associated with this notification. For example, the system or the UI notifies the eye gaze tracker 106 that the new image is loaded and displayed on the UI. The system creates a reference code, which includes a time stamp indicating the time the image is loaded on a display, and an identification of the image, e.g., the name associated with the image such as the name of the assessor (and/or name of a patient for a medical image). The eye-gaze tracker starts a new recording, creating an eye-gaze pattern detection session identified by the reference code for this image analysis by the expert.

An audio recorder such as a microphone 108 is notified that a new image is made available. This notification includes the associated reference code, for example, the same reference code associated with the notification received at the eye-gaze tracker. The audio recorder starts a new audio recording session for the image identified by the reference code, e.g., responsive to the notification.

The expert 104 by using the visual display on UI 102, enters or draws annotations for the given image. At the same time, the gaze-tracker and the audio recorder capture the expert's visual and audio feedback. The expert 104 interacts with the UI 102 to terminate and store the annotation into the system. The eye-gaze tracker completes the session recording. The audio recorder completes the session recording.

An eye-pattern-extractor 108 extracts the data points of the eye-gaze movements and timecodes them. For example, The eye movement is recorded by an eye-gaze tracker 106 with a specific frequency. An inbuilt software keeps track of which eye gaze instance corresponds to what time stamp (e.g., in terms of hh:mm:ss (hour, minute, second) extracted from the computer's CPU clock or the like). Based on the time stamp, the system of the present disclosure may synchronize the eye gaze instances with other input sources such as audio and image annotations.

A speech-recognition component 110 analyzes the audio data in the audio recorder session recording, and detects and timecodes key words that have been spoken by the expert. For example, the audio recorder is constantly recording data and synchronizing the recorded data with the time from the CPU clock. Thus, keywords spoken at specific instances have a time stamp that is synchronous with the eye gaze tracker's data, for example, eye gaze instance. As shown at 114, speech is converted to text including the timecoded key words.

An annotation extractor 112 analyzes the annotations that the expert 104 has made on the image. For example, the annotation drawn by the expert 104 by using the visual display on UI 102 and the image presented to the expert are read by the image annotation extractor 112. The annotation extractor then crops the region within the marked annotations from the image and sends it to the correlation module 116 together with the annotation coordinated and label. For example, if the expert annotated a rectangle (top-left-x:15, top-left-y:20, width-256, height-256) on image x1.jpeg, and gave it the label "hemorrhage" at time-10:30:00, the annotation extractor crops the appropriate region of the image and forwards the following massage to the correlation module [time: 10:30:00, image-name: x1.jpeg, image-data: <pixel values within the marked rectangle extracted from the image>, coordinates: (15,20), label: hemorrhage.

A correlation module 116 takes into account the following items: pre-existing knowledge in a knowledge base, which the correlation module uses to guide the mapping of time-coded input to the corresponding features or measurements; annotations and the time the annotations were entered by the expert, which are attached to the image; time-coded eye-gaze patterns extracted by the eye-pattern-extractor (e.g., eye data analyzer 108), time-coded key words spoken by the expert. The correlation module 116 correlates and cross-references this information, and enriches the metadata of the image into the knowledge base, by using as a key the reference code. Based on the time spent, the particular morphological features that the expert analyzes and pays most attention, the system of the present disclosure in one embodiment identifies regions that are interesting (e.g., showing an abnormality). The regions where the expert spends more time present greater ambiguity and are more difficult to identify and need to be given extra attention during learning, teaching and evaluation. Based on the time spent, the system groups these regions as obvious, less ambiguous and more ambiguous. In addition, by analyzing the time spent on specific morphologies, the system can learn characteristics of difficult examples. The reference code is used to ensure that the analysis of data from multiple sources is of an image with the same reference code. The output of this correlation module is a synchronous knowledge base that has correlated the extracted features and/or analysis with the corresponding time stamp to ensure that the metadata derived from each source is of the same image analyzed at the same time or time frame.

Knowledge Base Creation/Learning Module

The learning module, for example, the correlation module 116 captures knowledge on image analysis by a user (e.g., an expert user) and models the captured knowledge as a learning model to train other users to analyze the image. For example, the learning module captures knowledge on DR diagnosis and severity estimation from expert ophthalmologists and models it such that it can be used in effective training of new ophthalmologists and/or graders. The learning module presents fundus images to the expert ophthalmologists through an interface as shown in FIG. 1, and uses the following features as its input in building the knowledge base: image features, eye tracking data and audio cues.

At the completion of the learning phase, the system of the present disclosure in one embodiment will have generated the following representations: A set of learned dictionaries and/or convolutional filters that can distinguish between the following cases: clearly identifiable normal regions, clearly identifiable pathological regions, normal regions that were not easily identifiable, pathology regions that were not easily identifiable; eye tracking data depicting the analysis sequence followed by the expert, time spent examining each region; and a set of keywords and assertions used by the expert in describing the grading process.

Image Annotations

In one embodiment, the system of the present disclosure presents images to a user, for example, fundus images to an expert ophthalmologist case by case via a user interface 102. The user interface 102 allows the user to annotate the image, for example, by marking the image with an input device. The user, for example, expert ophthalmologists would then annotate regions on the image which shows signs of DR pathologies (such as micro-aneurysms, hemorrhages, neovascularization's) and provide a DR severity score. The learning module accumulates this information and analyzes a collection of such annotations, learning a model representation that best discriminates between regions of DR and non-DR. In one embodiment, the learning module may employ a deep learning architecture to model the image information which is parameterized by a set of learned convolutional filters. In one embodiment, classification approach using convolutional neural networks (CNNs) may be implemented for identifying microaneurysms (MAs). For example, the CNN architecture takes as input the image patches and the labels (for example, described above) that have been annotated by the expert, and based on the input, trains a deep neural network. The deep neural network has cropped image patches (pixel values within the annotated region) as the input and learns to predict a label similar to the label given by the expert as the ground-truth. The neural network can have multiple layers of convolution, max pooling, and activation, based on the architecture that gives the best performance. The updating of weights is done by back propagation of the error between the ground-truth label and the predicted labels. This model learning approach is different from the previous approaches that use hand engineered features to differentiate between DR and non-DR images. The learnt convolutional filters are used in teaching the user about highly discriminative patterns between DR and non-DR pathology, in one embodiment. The learnt convolutional features and/or maps can be applied to new images and the regions that cause these features to be activated to help a user to visualize which regions are important for a particular task (e.g., disease detection). The filters and/or convolution kernels that generate these visualizations can be used on new images to identify the regions that are most interesting.

Eye Tracking Data

As an example, when an expert ophthalmologist is presented with a fundus image, the expert uses his or her experience to direct his or her attention to specific regions on the image and analyzes those specific regions in detail to derive the correct conclusion. The system of the present disclosure is constructed such that it can capture this information and utilize it for training new ophthalmologists. During the learning phase, the system uses an eye-tracker to record the eye movement pattern of the expert. The eye-tracker records where the expert first looks at, and the subsequent regions he or she focuses attention. Human eye movement patterns can be either fixations or saccades. Fixations refer to those instances where the eye is focused on one particular location (and its immediate local neighborhood). Saccades refers to the transition movement of the eye from one location to another. The speed of the eye movement is higher during saccades than during fixations. Reliable algorithms exist to differentiate between fixations and saccades and can be used to identify fixated regions.

The system in one embodiment analyzes the eye fixation information for those regions annotated as having DR pathology by the expert. The system identifies the time spent, the particular morphological features that the ophthalmologist pays most attention and particularly extra attention given to specific areas. The time spent on an area will identify those which are easily identifiable as DR from those which present greater ambiguity. The second category of annotations that present greater ambiguity are the ones that are more difficult to identify and need to be given extra attention during learning, teaching and evaluation. Based on the time spent, the system of the present disclosure groups these regions as obvious, less ambiguous and more ambiguous. In addition, by analyzing the time spent on specific morphologies, the system can learn characteristics of difficult examples. A threshold time may be set or configured for determining whether an image is ambiguous or clearly identifiable. Typical threshold times may be in the range of 2-5 minutes. For example, if the expert spent more than 5 minutes looking at an image region, image characteristics in that region may be considered ambiguous. For example, while creating the knowledge base the expert is also providing the labels/disease class of that region, for example, via annotations and/or audio recording. The system in one embodiment clusters or groups each region based on the label provided by the expert. The system then calculates the time spent on each label by analyzing the time stamps of the eye-gaze recordings. The time value may function as an indicator of how much time an expert spends on different areas of varying severity. If more than one session's data (e.g., multiple experts' sessions, multiple sessions of the same expert) is used in learning, the average time spent on each label from multiple sessions may be computed and used as an indicator of how much time an expert spends on different areas of varying severity.

An eye tracking system or eye tracker may include a head mounted display and/or a web camera. The eye tracking system records the eye movement patterns of the expert as the expert analyzes the presented image and outputs the following information: temporal sequence of fixated regions, for example, in the data format comprising (time stamp, region identifier (ID)); and the time the expert spent in analyzing each region. Time spent in each region is determined by the eye fixation patterns. For example, inbuilt software in modern eye trackers can determine which instance is a fixation (i.e., the observer is closely examining the region), and which instance is a saccade (observer's eye is just passing over that region). When a number of fixations are concentrated on a region then the start and end time of that period is determined and the total spent is calculated. The time spent in analyzing each region may be determined by analyzing the temporal sequence of fixated regions. In one embodiment, the region ID is defined with respect to a normalized coordinate system that is consistent across fundus images from different patients.

A learning system of the present disclosure in one embodiment uses this information to model the expert search strategy for separate disease types and to predict the difficulty or importance of an image region in diagnosing a particular decease type. For example, the expert search strategy is modeled using recurrent neural networks. The eye tracking patterns can also be used to identify onset of fatigue in the expert. For example, when the expert starts to get tired his eye fixation is not steady and his eye gaze movement is beyond the normal acceptable range for normal gazing. For example, when an expert is experiencing fatigue then the recorded data may not be accurate, which may result in generating an accurate model. Therefore, the period of time during which an expert's gaze is associated with fatigue, may be discounted or not used as part of eye-gaze data in generating the knowledgebase or learning model.

Figure 6:
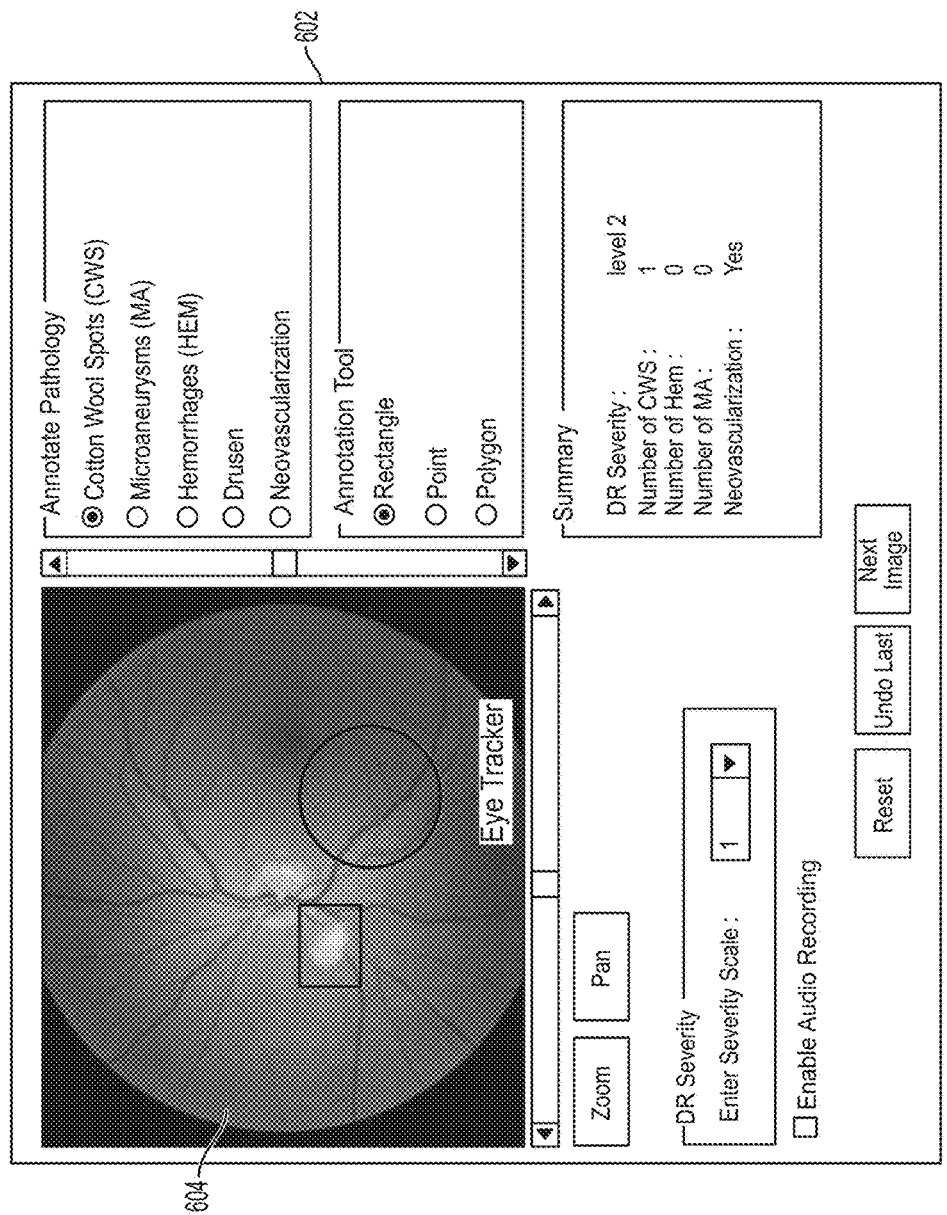
FIG. 6 illustrates a screenshot of a learning module in operation in one embodiment of the present disclosure.

FIG. 6 illustrates an example screenshot of a learning module in operation in one embodiment of the present disclosure. A user or an expert (e.g., as shown in FIG. 1) may be presented with an image on the user interface screen and allowed to enter annotations on the image. In addition, as described above, an eye tracker system monitors the user's eye pattern while the user is analyzing the image.

Audio Cues

The system of the present disclosure as shown in FIG. 1 may record any audio input provided by the expert, translate it to text and extract keywords that represent concepts and/or assertions from text. For instance, the output of the speech to text converter is processed by natural language processing algorithms to extract keywords. These keywords are recorded in the database in synchronization with the time stamp of the eye tracking data in order to identify the eye tracking instance to the corresponding audio input. For instance, the time of the audio recording, for example, the time the speech associated with an extracted keyword is uttered, is saved or stored as the corresponding time stamp of that keyword.

A user, for example, an expert ophthalmologist may also provide audio cues while annotating the images. Audio cues may include, but not limited to, information such as 1) regions that present difficulty and/or ambiguity in grading and why; 2) what kind of features and/or knowledge helped the ophthalmologist in resolving that ambiguity; 3) what to look out for in similar cases. A speech to text method converts the speech to text and extracts meaningful concepts from them. For example, a natural language processing algorithm may be utilized to extract keywords from the converted speech-to-text.

Figure 2:
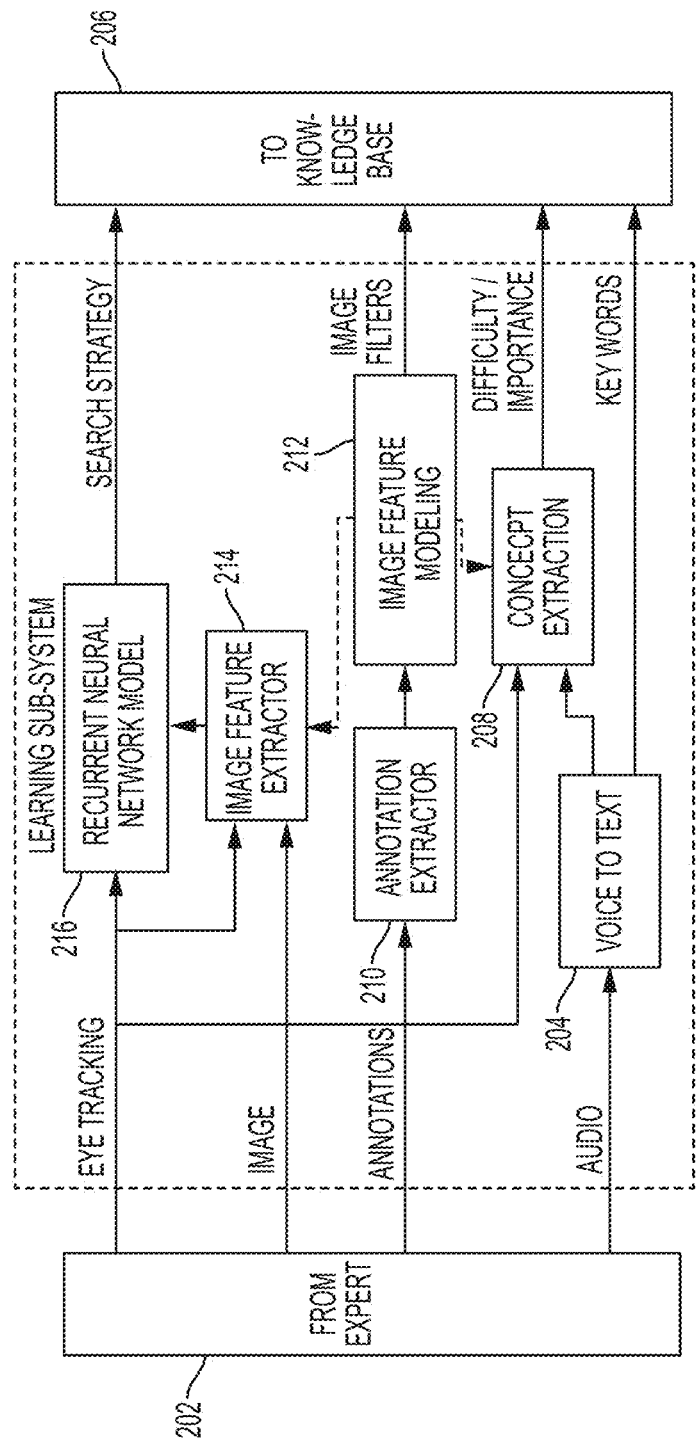
FIG. 2 is a diagram illustrating a learning system in one embodiment of the present disclosure.

FIG. 2 is a diagram illustrating a learning system in one embodiment of the present disclosure. The learning system receives inputs from different sources: eye tracking data, audio cues and image annotations. The learning system also receives image data, for example, from a knowledgebase or database of images. The different sources of data are received as a user or expert 202 inputs information while analyzing a presented image, for example, as described above with reference to FIG. 1. For example, eye tracking data is received from an eye tracking system that monitors the user's eye movement patterns on the image. Audio cues are received via a microphone to which the user may speak about the image the user is analyzing. Annotations are received via a UI receiving input signals from an input device by which the user may annotate the image on a display screen or device. Image data is received from a database of images. Voice to text component 204 translates the received audio data into text. Keywords are extracted from the translated text and saved in a knowledge base 106.

A concept extraction component 208 may receive the translated text from the voice to text component 204 and also the eye tracking data. For example, the concept extraction module 208 takes three messages (signals) as input: eye-tracking data, image features corresponding to an annotation and keyword text (keywords uttered by expert converted to text). This module 208 then attaches a difficulty and/or importance label (e.g., difficult to identify pathology in region, easy to identify pathology in region, region highly important for the diagnosis of the image, region of medium importance for image diagnosis, region of low importance for image diagnosis) to the image regions. The difficulty label (e.g., difficult to identify pathology in region, easy to identify pathology in region) is derived using the time spent on a region (e.g., difficult if the time spent on the region is greater than a specific threshold) gained through eye tracking, and keywords (e.g., a threshold number of keywords matched against a list of known words to describe difficulty). The importance labels are derived using keywords. Once the labels are derived they are coupled with the corresponding image features from 212 and are sent to the knowledge base 206.

An annotation extractor 210 (e.g., annotation extractor 112 shown in FIG. 1) extracts annotations made by the user from image. For example, the annotation extractor 210 performs the functions described above with respect to the annotation extractor 112 shown in FIG. 1, and derives an image region that is annotated by an expert. The annotation extractor 210 learns convolutions kernel representation of the annotated regions.

Image feature modeling component 212 takes the annotations extracted by the annotation extractor 210, and trains the CNN. The CNN outputs image filters, for example, convolution kernels. The output is stored in the knowledgebase 206.

Image feature extractor 214 uses the image filters learned by the module 212 to extract features from images at locations fixated by the expert (e.g., identified through eye tracking). The extracted features are then fed in to a recurrent neural network model 216.

Figure 4:
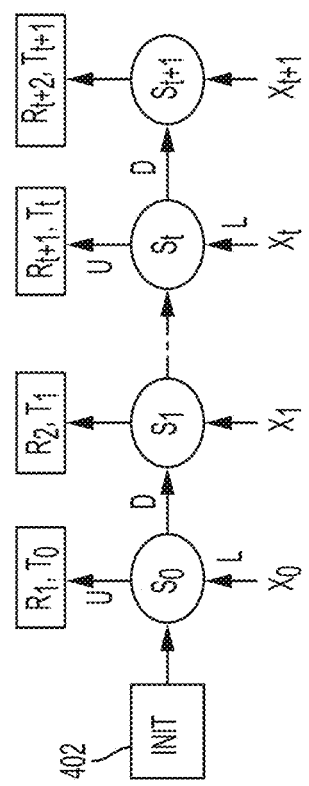
FIG. 4 is a diagram illustrating recurrent neural network architecture used in modeling the expert search sequence.

Recurrent neural network model 216 models eye pattern sequences. The recurrent neural network model 216 models a search sequence followed by the expert ophthalmologist so that the model can be used to show a student or the like, what the best search strategy would be for a given new image. The expert search sequence is modeled using recurrent neural network architecture. FIG. 4 is a diagram illustrating recurrent neural network architecture used in modeling the expert search sequence. In one embodiment, the model that evaluates the likelihood that a sequence would be followed by an expert is built as follows. The system extracts the features of each image region traversed by the expert in sequence (X0, X1, ..., Xt, ...). These features are extracted using the convolutional neural network filters learned through image annotations. The system also extracts the next image region visited by each expert and the time spent on each region as Ri+1, Ti (from eye tracking). The system then models the likelihood function, dynamic model and the output function using neural networks with weight matrix L, D, U respectively. Once the model is designed the modeling parameters L, D, U (weights of a neural network) are learned using the back propagation technique. The learned model is then saved in the knowledgebase 206 as show in the arrow "search strategy".

Figure 3:
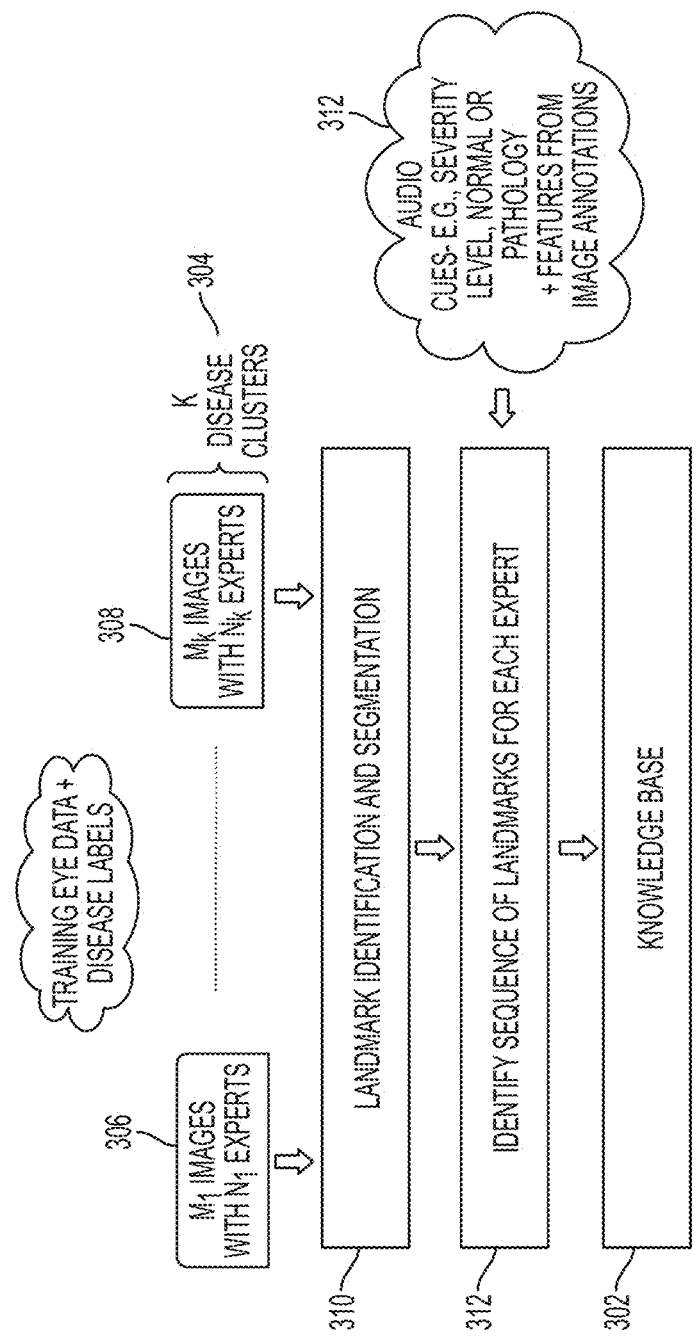
FIG. 3 is a diagram illustrating a workflow that maps eye scan patterns to disease specific behavior in one embodiment of the present disclosure.

Constructing the Knowledge Database
Identifying Disease Specific Eye Movement Pattern FIG. 3 is a diagram illustrating a workflow that maps eye scan patterns to disease specific behavior in one embodiment of the present disclosure. FIG. 3 shows another component of the system in one embodiment, which resides in the knowledge base. The components shown in FIG. 3 in one embodiment models the search strategy followed by the expert ophthalmologist in analyzing images that is of a specific disease type (e.g., severe diabetic retinopathy, macular edema, glaucoma). The knowledge base 302 records the eye movement of each ophthalmologist for each image analyzed. Since the disease labels for each image is known, the system of the present disclosure can map an eye movement sequence to a specific disease. For example, the disease labels are provided by the expert through speech where the expert may say "this region has this particular disease severity".

The system clusters the images into k different clusters (e.g., using k-means clustering) 304 based on the k disease labels. The corresponding eye movement patterns are grouped into these clusters. For every image in a specific cluster (e.g., 306, 308), there exists corresponding eye movement patterns from n experts, where n>=1, for example, as generated by the system of the present disclosure as described above. For each image, the system has a module that can segment and/or identify the different landmarks in the retinal images, such as fovea, macula, optic cup and disc, retinal vasculature as shown at 310. A known segmentation methodology may be used for segmenting or identifying different landmarks in images. Shown at 312, the system identifies a sequence of landmarks for each expert by mapping the location of the gaze in the eye-pattern with the landmarks identified at 310. Thus, the system can identify the landmarks corresponding to each fixation of the expert, and map the sequence of fixated landmarks by an expert to the corresponding disease label. For example, given an input image, the system in one embodiment of the present disclosure segments the image into its constituent landmarks. As the system records the expert's observations it also correlates which landmark the expert observed at which point in time. Thus, the sequence of landmarks viewed provides that, for example, for diabetic retinopathy the expert first looks at optic disc, then fovea and then the optic cup.

If there is more than one expert, the system in one embodiment determines the fixation sequence of each expert and compares the landmarks they examined. If the sequence of landmarks visited is the same by all experts then there are no ambiguities. However if the sequences of landmarks examined by different experts in a particular image do not agree then the system may take the sequence with the majority vote, e.g., with the most number of agreements. Once the system has determined the sequence of landmarks, the system identifies the center of each landmark as the point of examination.

In one embodiment, additional keywords and assertions are tagged to the corresponding fixations. Such data, for example, may have been stored and received from a network 312. The keywords from audio input are used to identify a particular fixated region as either normal or having pathologies. The corresponding eye fixation patterns are then analyzed to learn a set of image feature representations such as convolutional filters that can optimally distinguish between normal regions and pathological regions with different levels of severity. The audio cues may be also used to identify the severity level of a particular region. For example, severity level of region is given by the expert in the audio. The data also may include image annotations, used to identify the severity level of a particular region.

At the completion of the learning phase, the following representations are generated: a set of learned convolutional filters (also referred to as dictionaries) that can distinguish between the following cases: clearly identifiable normal regions, clearly identifiable pathological regions, normal regions that were not easily identifiable, pathology regions that were not easily identifiable; eye tracking data depicting the analysis sequence followed by the expert and time spent examining each region; a set of keywords and assertions used by the experts in describing a grading process.

Normalized Coordinate System and Region ID:

The system of the present disclosure may generate a location coordinate structure that defines regions that are consistent with the anatomical structure of the eye. Each individual digital fundus image may be slightly rotated or shifted due to discrepancies during the image capture or structural variations. If the device coordinate system is used directly, the region IDs may not correspond to anatomical regions. For example, in one image fovea would be in region i and in the next image it may be in region j.

In one embodiment, the system of the present disclosure defines a normalized coordinate system as follows. An example is given with an image of fundus. However, the normalized coordinate system may be generated with respect to any other image. The system identifies the optic disk centre and the fovea location of the fundus image. The origin of the coordinate system is defined as the optic disc centre and the x axis is in the direction that travels from the optic disk centre towards the fovea. The y axis is defined to form a write handed system. The units are such that the distance between optic disc centre and the fovea is one. The system in one embodiment uses this anatomically consistent coordinate system to define a set of K fixed regions.

In one embodiment, the system models an expert image analysis sequence using recurrent neural network architecture. The system builds a model that captures the search pattern followed by the expert so that if a new image search sequence is given for a particular image, the system is able to evaluate how likely that sequence would be followed by an expert. The search pattern here refers to the sequence of locations the expert fixated the expert's eye-gaze during the expert's analysis of the image and the time the expert's eye-gaze was fixated to the particulate region (e.g., the information derived from eye tracking). An example search sequence may be: {start, (location:(10,20), time:30s), (location:(50,25), time:10s), (location:(100,200), time:5s), (location:(150,25), time:3s), end}. The model allows the system to generate high probable search sequences, such that if given a new image that is not analyzed by an expert, the system is able to derive a search sequence that is likely to be followed by an expert.

In one embodiment, the expert search sequence is modeled using recurrent neural network architecture. FIG. 4 is a diagram illustrating recurrent neural network architecture used in modeling the expert search sequence. In one embodiment, the model that evaluates the likelihood that a sequence would be followed by an expert is built as follows. The system extracts the features of each image region traversed by the expert in sequence (X0, X1, . . . , Xt, . . . ). These features are extracted using the convolutional neural network filters learned through image annotations. The system also extracts the next image region visited by each expert and the time spent on each region as $R_{i+1}$, $T_i$. The system then models the likelihood function, dynamic model and the output function using neural networks with weight matrix L, D, U respectively. Once the model is designed the modeling parameters L, D, U (weights of a neural network) are learned using the back propagation technique.

An example likelihood function may include: t=current step index;
X(t)=features extracted from region the expert is fixated at step t;
R(t+1)=region coordinates the expert would fixate next (predicted output at step t in recurrent neural network, part one);
T(t)=time expert will spend at region t (predicted output at step t in recurrent neural network, part two);
S(t)=hidden state vector at step t;
Sig=sigmoid activation function;
St=Sig(D*S(t−1)+L*X(t));
[R(t+1), T(t)]=Sig(U*S(t)). For convenience the bias vectors are not shown but each matrix may include a bias component.

The block init 402 produces an initial state from a learned distribution based on the decided pattern.

Modeling image difficulty or importance finds a low dimensional embedding such that similar images (e.g., in terms of difficulty to diagnose, importance for learner) are close together. When such an embedding is found, the system can use it to query images that are similar or dissimilar to a reference image and also use the embedding to identify clusters such as easy, medium or difficult to diagnose. The system may use following information as input features for this embedding mechanism: Image features extracted through convolutional neural networks learned using image annotation by experts; Keywords extracted by voice to text conversion of expert audio cues; Time spent on image regions obtained by expert eye tracking. In one embodiment, the system may collect the above information as features for each expert annotated image and use the t-SNE algorithm to convert them to an n-dimensional embedding. The low dimensional features are then stored in the knowledge base and k-means clustering is used to obtain the cluster of images that has similar difficulty based on expert keywords as guides. K nearest neighbor's algorithm is used to query images that are similar to a particular image. Modeling image difficulty, for example, determines the difficulty level, e.g., easy, medium or difficult of diagnosing the image based on image similarity.

In one embodiment of the present disclosure, eye tracking data, image annotations, and audio cues are employed in analyzing image features to identify different regions or pathologies in an image. For example, the system of the present disclosure in one embodiment determines the thinking of an expert based on eye tracking analysis and audio cues. The system learns the scientific sequence of steps employed by a human expert to analyze and interpret an image. The system in one embodiment models the eye tracking using a recurrent neural network (RNN). This is helpful in predicting fixations and understanding the context under which a specific scan pattern was followed.

Figure 7:
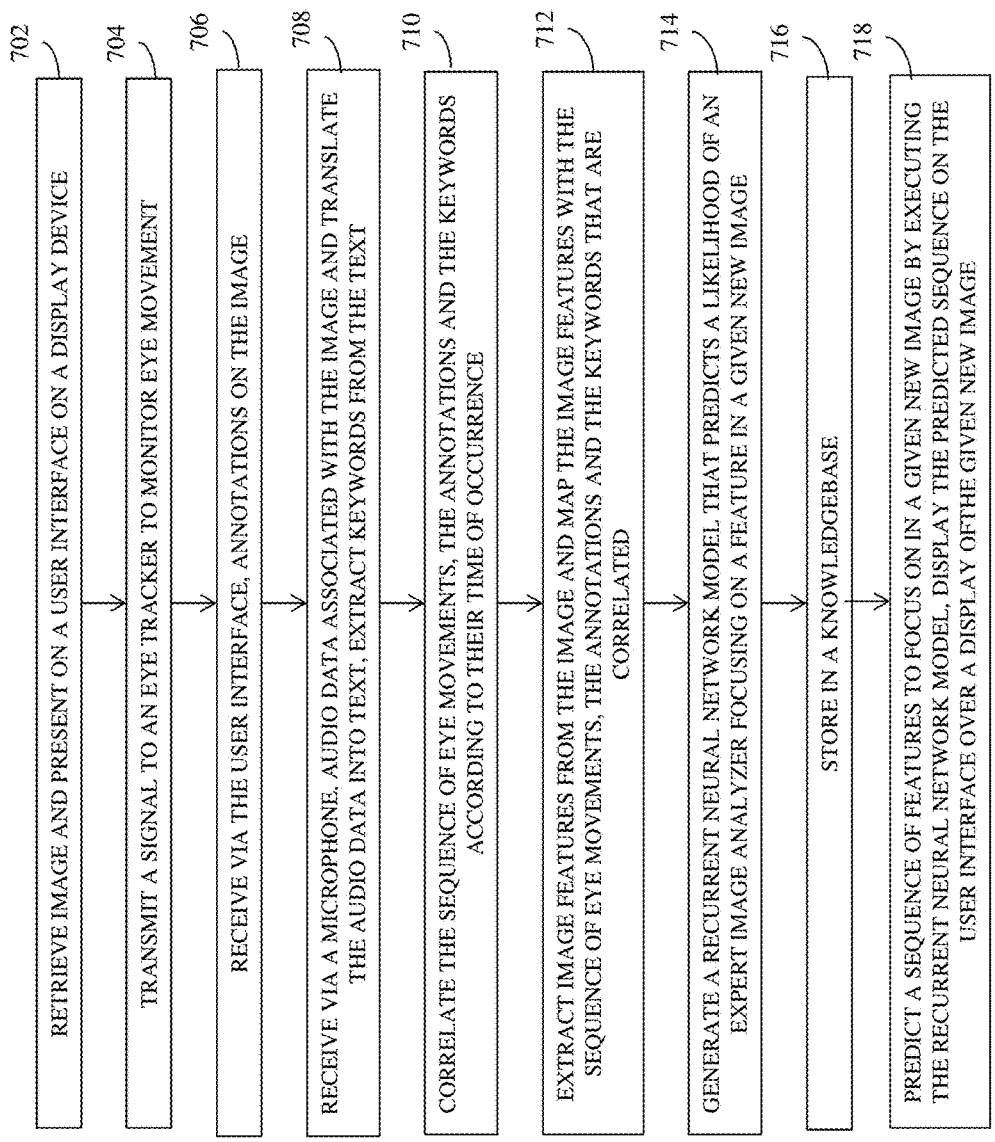
FIG. 7 is a flow diagram illustrating an overview of a method in one embodiment of the present disclosure.

FIG. 7 is a flow diagram illustrating an overview of a method in one embodiment of the present disclosure. At 702, the method may include retrieving an image from a database of images and presenting the image on a user interface displayed on a display device. At 704, a signal is transmitted to an eye tracker comprising at least a camera coupled to the hardware processor, the signal representing a notification to the eye tracker to monitor eye movements of a user analyzing the image and generating a sequence of eye movements based on the eye tracker monitor the eye movements. At 706, via the user interface, annotations on the image input by the user are received. At 708, via a microphone coupled to the hardware processor, audio data associated with the image spoken by the user is received. The audio data is translated into text, and keywords are extracted from the text. At 710, the method may include correlating the sequence of eye movements, the annotations and the keywords according to their time of occurrence. At 712, image features are extracted from the image and mapped with the sequence of eye movements, the annotations and the keywords that are correlated. At 714, a recurrent neural network model is generated that predicts a likelihood of an expert image analyzer focusing on a feature in a given new image. The recurrent neural network model is generated based on mappings of the image features with the sequence of eye movements, the annotations and the keywords that are correlated. At 716, the recurrent neural network model and the mappings of the image features with the sequence of eye movements, the annotations and the keywords that are correlated, are stored in a knowledgebase. At 718, a sequence of features to focus on in a given new image may be predicted by executing the recurrent neural network model. The predicted sequence or path may be displayed on the user interface over a display of the given new image.

In previous works using eye tracking, the scope of feedback and improvement is limited to those cases that are part of the training data set diagnosed by the expert. Such system may not be able to cope with new images that present novel scenarios, features, and/or characteristics. In the previous works, a significant part of the learning is based on simulated scenarios. Although these scenarios are based on past real world scenarios they are implemented in a controlled environment which may not perform well for real world cases, especially when there is no expert image analyst to evaluate user performance. The previous works also do not leverage image information and audio cues to adapt a teaching process. Those previous works do not extract image information to improve a training or teaching module.

The system of the present disclosure in one embodiment models knowledge of a user or expert from multiple sources. The system creates a knowledge base that combines knowledge from eye tracking, image annotations and audio cues. In one embodiment, the system correlates information from multiple sources through the use of neural networks and machine learning algorithms. The learnt knowledge can be visualized in the form of learned filters (also referred to as convolutional kernels), audio cues and context of eye scanning patterns.

Figure 5:
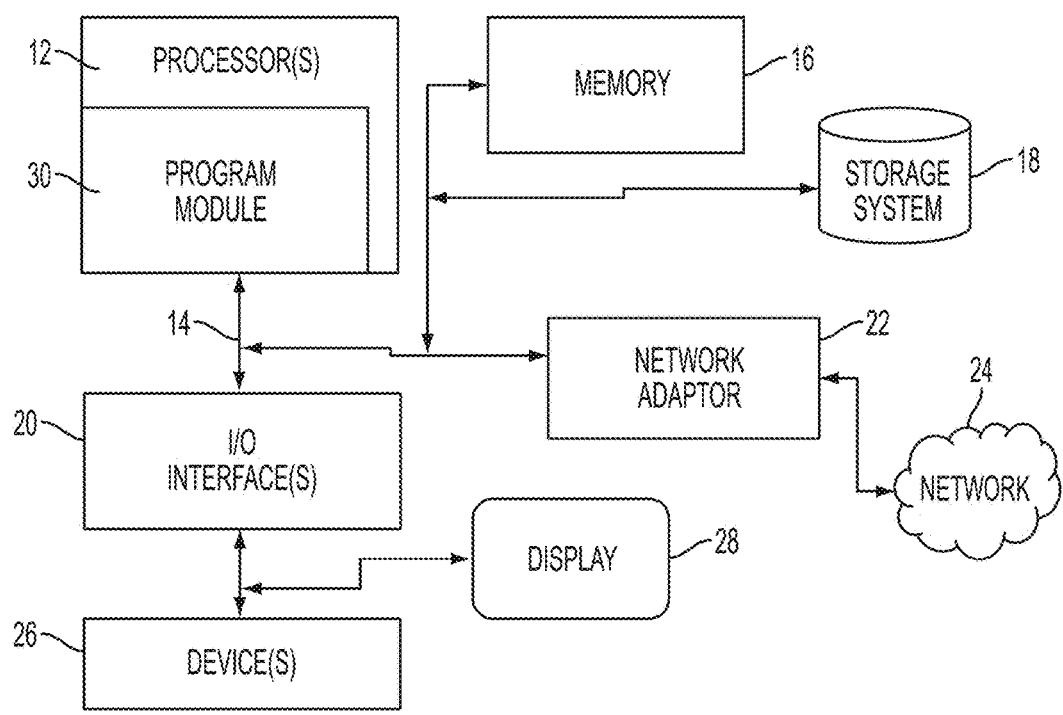
FIG. 5 illustrates a schematic of an example computer or processing system that may implement a knowledgebase construction system in one embodiment of the present disclosure.

FIG. 5 illustrates a schematic of an example computer or processing system that may implement a knowledgebase construction system in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 5 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a module 30 that performs the methods described herein. The module 30 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

We claim:

1. A system of generating a knowledge base from annotated images, comprising:
   a hardware processor executing a user interface, the hardware processor retrieving an image from a database of images and presenting the image on the user interface displayed on a display device;
   an eye tracker comprising at least a camera and coupled to the hardware processor, the eye tracker monitoring eye movements of a user analyzing the image and generating a sequence of eye movements;
   the user interface receiving annotations on the image input by the user;
   a microphone coupled to the hardware processor;
   the hardware processor receiving via the microphone audio data associated with the image spoken by the user, the hardware processor translating the audio data into text, the hardware processor extracting keywords from the text;
   the hardware processor correlating the sequence of eye movements, the annotations and the keywords according to their time of occurrence;
   the hardware processor extracting image features from the image and mapping the image features with the sequence of eye movements, the annotations and the keywords that are correlated;
   the hardware processor generating a recurrent neural network model that predicts a likelihood of an expert image analyzer focusing on a feature in a given new image,
   the hardware processor generating the recurrent neural network model based on mappings of the image features with the sequence of eye movements, the annotations and the keywords that are correlated; and
   a knowledgebase storing the recurrent neural network model and the mappings of the image features with the sequence of eye movements, the annotations and the keywords that are correlated.

2. The system of claim 1, wherein the image features are labeled with disease labels, wherein based on the disease labels, the recurrent neural network model autonomously identifies a region in the given new image associated with a probable disease.

3. The system of claim 2, wherein the hardware processor generates a location coordinate system definition associated with the image for mapping the image features in the image with the sequence of eye movements, the location coordinate system defined by identifying an optical optic disk center and a fovea location of a fundus in the image, and defining an x-axis in a direction from the optic disk center to the fovea, and a y-axis perpendicular to the x-axis, the origin of the x-axis defined by the optical optic disk center, and a unit of the coordinate system is defined as a distance between the optic disc center and the fovea.

4. The system of claim 1, wherein the recurrent neural network model is generated based on monitoring multiples users analyzing multiples of images.

5. The system of claim 1, wherein the recurrent neural network model, given the new image, predicts a sequence of image features in the new image the expert image analyzer would follow in analyzing the new image.

6. The system of claim 1, wherein the hardware processor extracting image features comprises the hardware processor training a convolutional neural network model to learn convolutional filters that recognize the image features, and executing the convolutional neural network that is trained to extract the image features.

7. The system of claim 6, wherein the convolutional neural network is trained to learn convolutional filters that distinguish identifiable regions and ambiguous regions in the given new image.

8. The system of claim 1, wherein the hardware processor further determines time spent by the user on the image features that are mapped, and based on the time spent, predicts whether an image feature is ambiguous or clearly identifiable.

9. A method of generating a knowledge base from annotated images, the method performed by at least one hardware processor, the method comprising:
   retrieving an image from a database of images and presenting the image on a user interface displayed on a display device;
   transmitting a signal to an eye tracker comprising at least a camera coupled to the hardware processor, the signal representing a notification to the eye tracker to monitor eye movements of a user analyzing the image and generating a sequence of eye movements based on the eye tracker monitor the eye movements;
   receiving via the user interface, annotations on the image input by the user;
   receiving via a microphone coupled to the hardware processor, audio data associated with the image spoken by the user, and translating the audio data into text, and extracting keywords from the text;
   correlating the sequence of eye movements, the annotations and the keywords according to their time of occurrence;
   extracting image features from the image and mapping the image features with the sequence of eye movements, the annotations and the keywords that are correlated;
   generating a recurrent neural network model that predicts a likelihood of an expert image analyzer focusing on a feature in a given new image, the generating the recurrent neural network model based on mappings of the image features with the sequence of eye movements, the annotations and the keywords that are correlated; and storing in a knowledgebase, the recurrent neural network model and the mappings of the image features with the sequence of eye movements, the annotations and the keywords that are correlated.

10. The method of claim 9, further comprising:
receiving the given new image; and
predicting by the recurrent neural network model executing on the hardware processor, a sequence of image features in the new image the expert image analyzer would follow in analyzing the new image.

11. The method of claim 9, wherein the image features are labeled with disease labels, wherein based on the disease labels, the recurrent neural network model autonomously identifies a region in the given new image associated with a probable disease.

12. The method of claim 11, further comprising generating a location coordinate system definition associated with the image for mapping the image features in the image with the sequence of eye movements, the location coordinate system defined by identifying an optical optic disk center and a fovea location of a fundus in the image, and defining an x-axis in a direction from the optic disk center to the fovea, and a y-axis perpendicular to the x-axis, the origin of the x-axis defined by the optical optic disk center, and a unit of the coordinate system is defined as a distance between the optic disc center and the fovea.

13. The method of claim 9, wherein the recurrent neural network model is generated based on monitoring multiples users analyzing multiples of images.

14. The method of claim 9, wherein the extracting of the image features comprises the training a convolutional neural network model to learn convolutional filters that recognize the image features, and executing the convolutional neural network that is trained to extract the image features.

15. The method of claim 14, wherein the convolutional neural network is trained to learn convolutional filters that distinguish identifiable regions and ambiguous regions in the given new image.

16. The method of claim 9, further comprising determining time spent by the user on the image features that are mapped, and based on the time spent, predicts whether an image feature is ambiguous or clearly identifiable.

17. A computer readable storage device storing a program of instructions executable by a machine to perform a method of generating a knowledge base from annotated images, the method comprising:
retrieving an image from a database of images and presenting the image on a user interface displayed on a display device;
transmitting a signal to an eye tracker comprising at least a camera coupled to the hardware processor, the signal representing a notification to the eye tracker to monitor eye movements of a user analyzing the image and generating a sequence of eye movements based on the eye tracker monitor the eye movements;
receiving via the user interface, annotations on the image input by the user;
receiving via a microphone coupled to the hardware processor, audio data associated with the image spoken by the user, and translating the audio data into text, and extracting keywords from the text;
correlating the sequence of eye movements, the annotations and the keywords according to their time of occurrence;
extracting image features from the image and mapping the image features with the sequence of eye movements, the annotations and the keywords that are correlated;
generating a recurrent neural network model that predicts a likelihood of an expert image analyzer focusing on a feature in a given new image, the generating the recurrent neural network model based on mappings of the image features with the sequence of eye movements, the annotations and the keywords that are correlated; and
storing in a knowledgebase, the recurrent neural network model and the mappings of the image features with the sequence of eye movements, the annotations and the keywords that are correlated.

18. The computer readable storage device of claim 17, further comprising:
receiving the given new image; and
predicting by the recurrent neural network model executing on the hardware processor, a sequence of image features in the new image the expert image analyzer would follow in analyzing the new image.

19. The computer readable storage device of claim 17, wherein the image features are labeled with disease labels, wherein based on the disease labels, the recurrent neural network model autonomously identifies a region in the given new image associated with a probable disease.

20. The computer readable storage device of claim 17, further comprising determining time spent by the user on the image features that are mapped, and based on the time spent, predicts whether an image feature is ambiguous or clearly identifiable.

* * * * *